US008176918B2

(12) United States Patent
Teng

(10) Patent No.: US 8,176,918 B2

(45) Date of Patent: May 15, 2012

(54) THREE DIMENSIONAL FACE MASK

(76) Inventor: Mei-Sheng Teng, Kowloon (CN)

( * ) Notice: Subject to any disclaimer, the term of this patent is extended or adjusted under 35 U.S.C. 154(b) by 244 days.

(21) Appl. No.: 12/778,370

(22) Filed: May 12, 2010

(65) Prior Publication Data

US 2011/0277769 A1 Nov. 17, 2011

(51) Int. Cl.
*A61M 11/00* (2006.01)

(52) U.S. Cl. ......... 128/206.19; 128/206.16; 128/206.17; 128/206.12

(58) Field of Classification Search ............. 128/206.19, 128/206.12, 205.29, 206.13, 206.16, 206.17, 128/206.18, 206.25
See application file for complete search history.

(56) References Cited

U.S. PATENT DOCUMENTS 2,228,218 A * 1/1941 Schwartz ................. 128/206.19
4,600,002 A * 7/1986 Maryyanek et al. ..... 128/206.19
4,739,755 A * 4/1988 White et al. ............. 128/206.12
5,003,633 A * 4/1991 Itoh ........................................ 2/9
5,307,796 A * 5/1994 Kronzer et al. .......... 128/206.16
6,102,039 A * 8/2000 Springett et al. ......... 128/206.12
2004/0011362 A1* 1/2004 Angadjivand et al. ... 128/206.13
2006/0254591 A1* 11/2006 Marx ....................... 128/206.19

* cited by examiner

*Primary Examiner* — Steven Douglas

(57) ABSTRACT

A three dimensional face mask comprises: a three dimensional cup, a three dimensional soft rubber washer, an elastic tape, and an anti-skid band; it is characterized in that: the three dimensional cup is made by hot pressing of multilayer of filtration material, the three dimensional soft rubber washer is provided with a soft nose cushion and is bonded to an outer periphery of the three dimensional cup by hot pressing, the anti-skid band is bonded to a lower edge of the three dimensional cup, the elastic tape has two ends symmetrically bonded to both sides of the three dimensional cup. The three dimensional non-woven face ensures a good air tightness against the face while leaving a large enough space between the three dimensional cup and the nose and mouth area to ensure conformable wearing, good filtration, making the wearer easy to breathe and talk.

7 Claims, 5 Drawing Sheets

THREE DIMENSIONAL FACE MASK

BACKGROUND OF THE INVENTION

1. Field of the Invention

The present invention relates to a face mask, and more particularly to a three dimensional non-woven face mask providing protection from bacteria and dust.

2. Description of the Prior Art

Non-woven face masks are widely used in medical facilities, food production factories, precision instruments manufacturing industry and other sites requiring high sanitation. Even in public places, more and more people are wearing face mask. Nowadays, face masks are used not only as medical products but also as daily commodities, and peoples' requirements to the face mask is becoming more and more strict. Hence, the practical, economic, safety, aesthetic and comfortable properties of the face mask are very important.

So far, the existing non-woven face masks are mostly two dimensional, and in order to ensure a good filtration effect, the ends of the two dimensional face masks have to be fastened tightly to the wearer's ears or head, so that the wearer may feel difficult to breathe and talk, the ears may feel unconformable, and the face may feel difficult to sweat. If such a face mask is worn by a wearer wearing glasses, the wearer's breath will flow through the clearance between the upper portion of the face mask and the face of the wearer to the wearer's glasses, causing foggy glasses.

The present invention has arisen to mitigate and/or obviate the afore-described disadvantages.

SUMMARY OF THE INVENTION

The primary object of the present invention is to provide a three dimensional non-woven face mask which ensures a good air tightness against the face while leaving a large enough space between the three dimensional cup and the nose and mouth area to ensure conformable wearing, good filtration, making the wearer easy to breathe and talk. To achieve this object, a three dimensional face mask provided by the present invention comprises: a three dimensional cup, a three dimensional soft rubber washer, an elastic tape, and an anti-skid band; it is characterized in that: the three dimensional cup is made by hot pressing of multilayer of filtration material, the three dimensional soft rubber washer is provided with a soft nose cushion and is bonded to an outer periphery of the three dimensional cup by hot pressing, the anti-skid band is bonded to a lower edge of the three dimensional cup, the elastic tape has two ends symmetrically bonded to both sides of the three dimensional cup.

When the face mask is worn, a large enough space will left between the three dimensional cup and the nose and mouth area, the soft nose cushion is fixed to a middle of an upper side of the three dimensional soft rubber washer, and a shape of the three dimensional soft rubber washer is similar to an outline of the face of a wearer, plus the three dimensional soft rubber washer has a high elasticity, making the three dimensional soft rubber washer fit snugly against the face and nose bridge of the wearer, while snuggly wrapping around the portion of the nose above the nose tip. Furthermore, anti-skid band is bonded to the lower edge of the three dimensional cup to naturally form a pocket-like structure which will fit snugly against the wearer's chin with the help of the elastic tape, so as to prevent the cap from sliding and facilitate comfortable and stable wearing of the face mask.

As compared with the traditional face mask, the face mask of the present invention provides a good air tightness against the face and comfortable wearing by solving the problem of poor airtightness caused by the uneven outline of the nose and face.

Obviously, the present invention has the advantages of simple structure, practical, comfortable wearing, good air tightness and infiltration while allowing the wearer to easily breathe and talk.

BRIEF DESCRIPTION OF THE DRAWINGS

FIG. 2-1 is a side view of the three dimensional face mask in accordance with the present invention;

FIG. 2-2 is a perspective view of the three dimensional face mask in accordance with the present invention;

FIG. 3-1 is a perspective view of a three dimensional cap of the three dimensional face mask in accordance with the present invention;

FIG. 3-2 is a front view of the three dimensional cap of the three dimensional face mask in accordance with the present invention;

FIG. 3-3 is a top view of the three dimensional cap of the three dimensional face mask in accordance with the present invention;

FIG. 4-1 is a side view of a three dimensional soft rubber washer in accordance with the present invention;

FIG. 4-2 is a front view of the three dimensional soft rubber washer in accordance with the present invention;

FIG. 4-3 is a perspective view of the three dimensional soft rubber washer in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Figure 1:
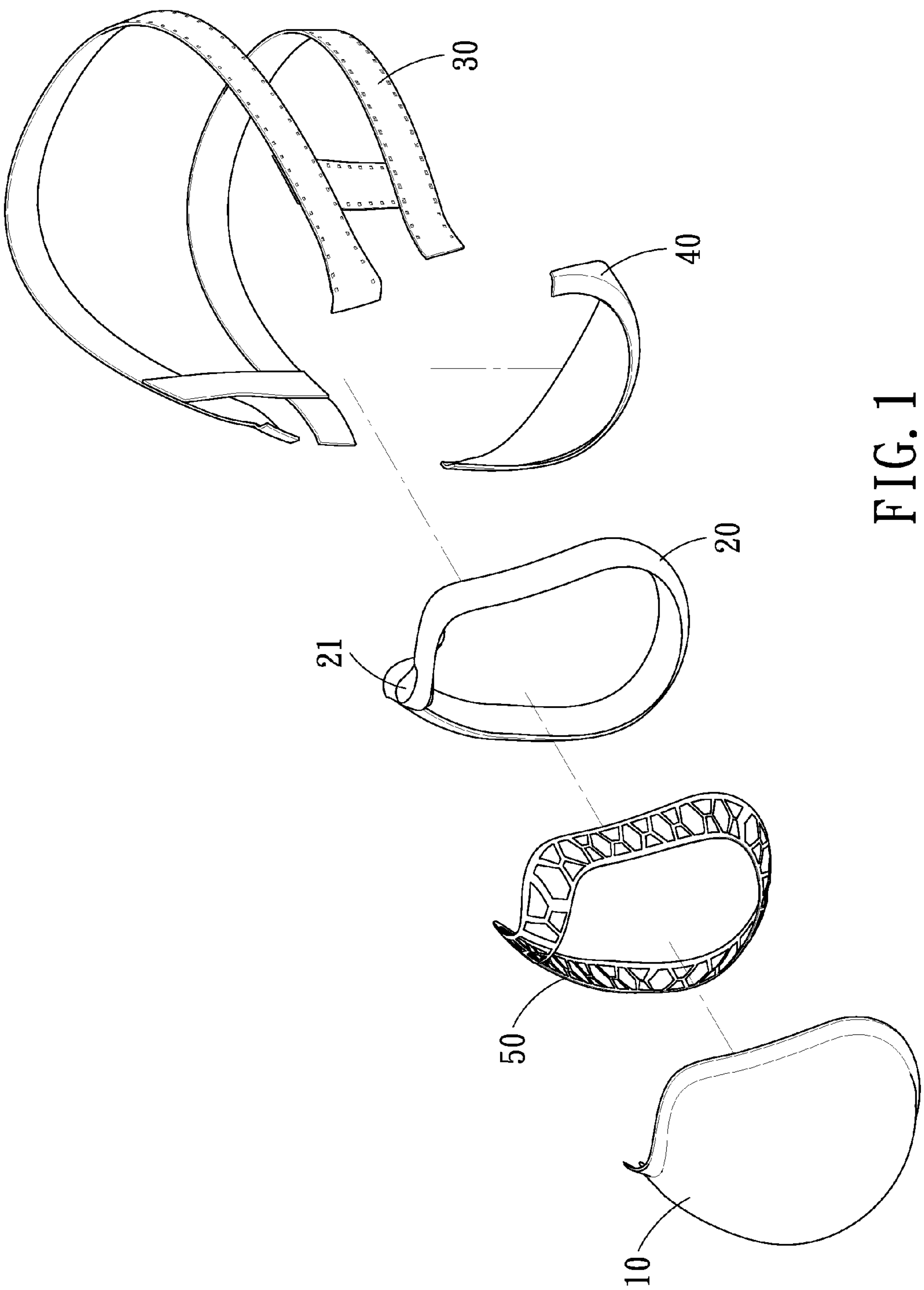
FIG. 1 is an exploded view of a three dimensional face mask in accordance with a preferred embodiment of the present invention.
Figure 2:
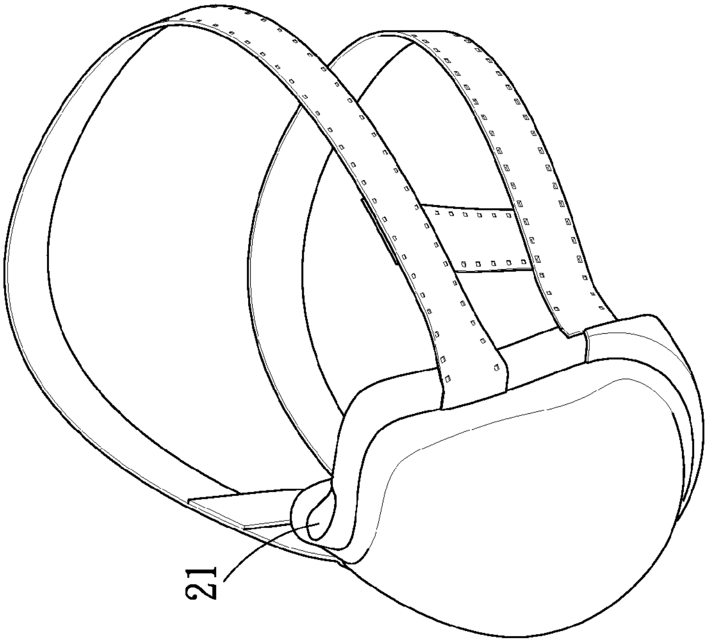
Figures 1, 2:
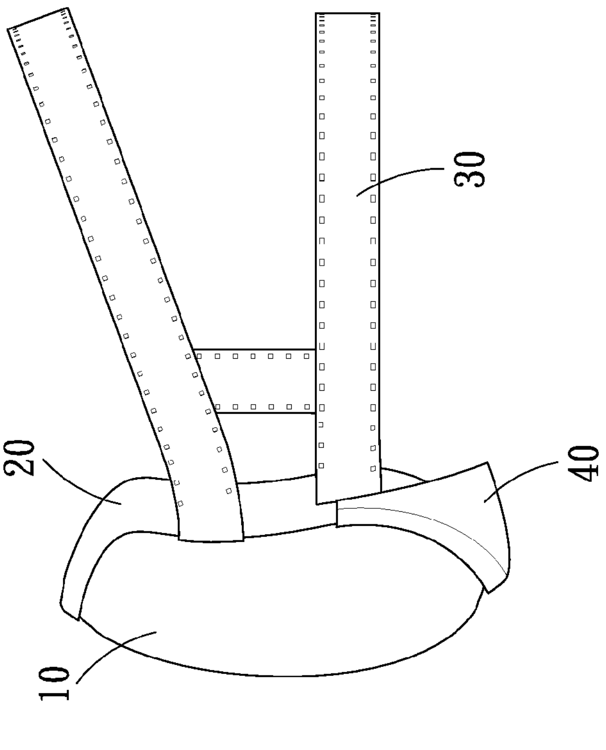

Referring to FIGS. 1, 2-1 and 2-2, a three dimensional face mask in accordance with a preferred embodiment of the present invention comprises a three dimensional cup 10, a three dimensional soft rubber washer 20, an elastic tape 30, an anti-skid band 40, and a support frame 50. The outer periphery of the three dimensional cup 10 which is made by hot pressing of multilayer of filtration material, and the three dimensional soft rubber washer 20 are bonded to the periphery of the elastic tape 30 by hot pressing. The anti-skid band 40 is bonded to the lower edge of the three dimensional cup 10. The support frame 50 is made of Polypropylene material with high elasticity and formed corresponding to the shape of the outer periphery of the three dimensional cup 10 so that the support frame 50 snuggly fits in the three dimensional cup 10, providing support for the three dimensional cup 10 and maintaining the shape of the three dimensional cup 10, making the three dimensional cup 10 return to its original shape easily after being pressed. The elastic tape 30 is H-shaped and has two ends symmetrically bonded to both sides of the three dimensional cup 10.

The elastic tape 30 is made of material with high elasticity, so that it can be slightly pulled over the back of the wearer's head. The anti-skid band 40 takes the form of a wide band and is bonded to the lower edge of the three dimensional cup 10 to naturally form a pocket-like structure which will fit snugly against the wearer's chin when the face mask is worn, so as to prevent the cap 10 from sliding and facilitate comfortable and stable wearing of the face mask.

Figure 3:
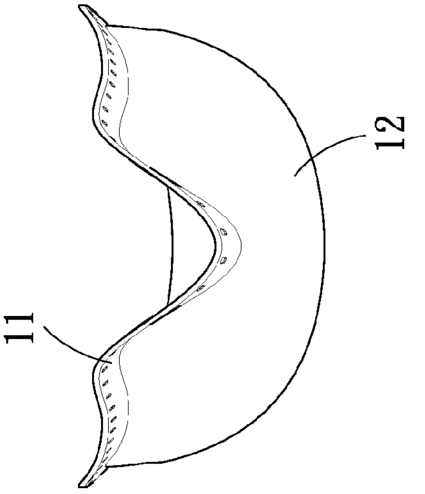
Figures 2, 3:
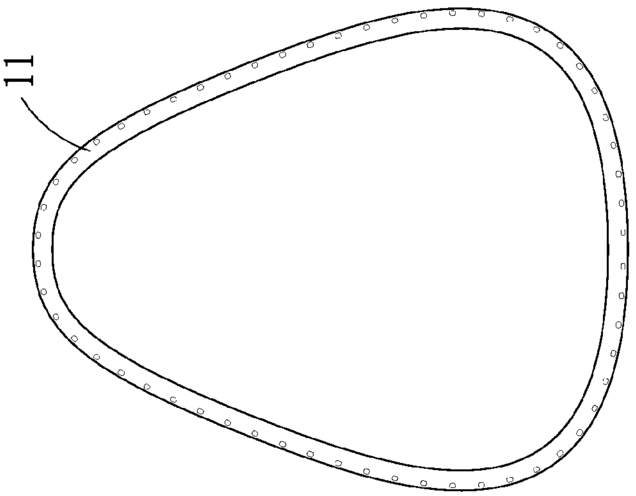
Figures 1, 3:
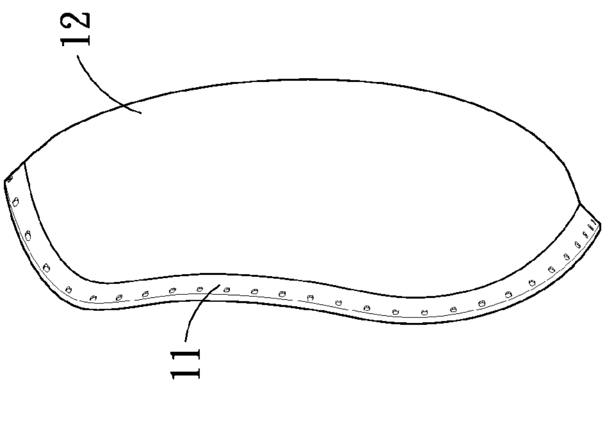
Figures 3, 4:
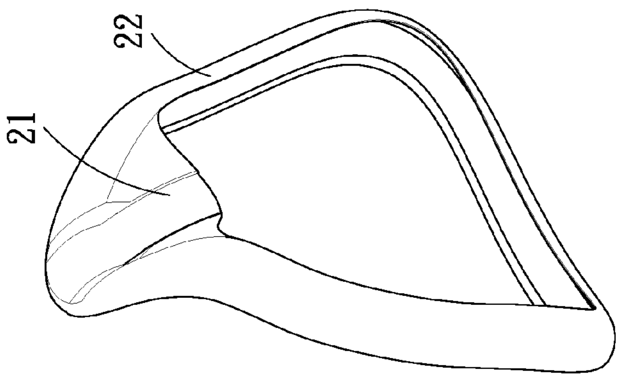
Figures 2, 4:
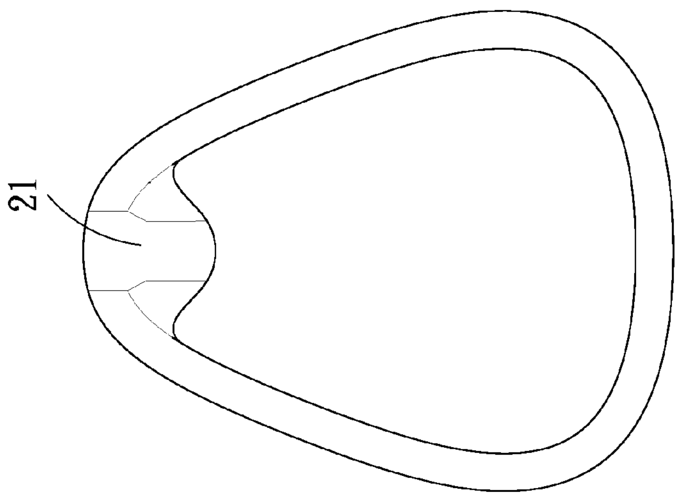
Figures 1, 4:
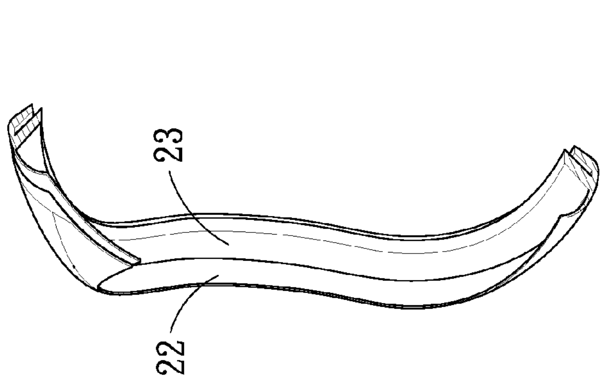

Referring then to FIGS. 3-1, 3-2 and 3-3, the three dimensional cup 10 which is made by hot pressing multilayer of non-woven filtration fabric together into a three dimensional shape. From front view, the shape of the three dimensional cup 10 is similar to the shape of the triangular area of the nose and mouth of the wearer, and from side view, the shape of the three dimensional cup 10 conforms to the outline of wearer's nose and mouth. The thickness of the filtration layer is determined by filtration function and the number of layers of the filtration material. The middle portion 12 of the three dimensional cup 10 is protruded outward, so that the outer peripheral edge of the three dimensional cup 10 is shaped in a three dimensional manner in the outline of the nose and mouth area, leaving a large enough space between the three dimensional cup 10 and the nose and mouth area to ensure conformable wearing, good filtration, making the wearer easy to breathe and talk.

Referring then to FIGS. 4-1, 4-2 and 4-3, the three dimensional soft rubber washer 20 in accordance with the present invention is a ring-shaped structure made by plastic injection. From front view, the shape of the three dimensional soft rubber washer 20 is similar to the shape of the triangular area of the nose and mouth of the wearer, and from side view, the shape of the three dimensional soft rubber washer 20 conforms to the outline of wearer's nose and mouth. The outer peripheral edge 23 of the three dimensional soft rubber washer 20 is bonded to the periphery 11 of the three dimensional cup 10 by hot pressing. The structure of the outer peripheral edge 23 and a contacting surface 22 (for contacting the wearer's face) of the three dimensional soft rubber washer 20 conform to the peripheral structure of the nose and mouth of the wearer. When the face mask is worn, the contacting surface 22 fits snuggly against the face of the wearer with the help of the elastic tape 30, ensuring an ideal air tightness against the face and a comfortable wearing.

To the middle of the upper side of the three dimensional soft rubber washer 20 is fixed a soft nose cushion 21 which is laminated and made by plastic injection simultaneously with the three dimensional soft rubber washer 20. When the wearer wears the face mask, the soft nose cushion 21 will snuggly wrap around the portion of the nose above the nose tip, ensuring a super air tightness effect, solving the problem of poor airtightness caused by the uneven outline of the nose and face and the problem of foggy glasses. Especially, doctors wearing glasses won't have foggy glasses, and thus reducing medical mistakes during operation.

Figure 5:
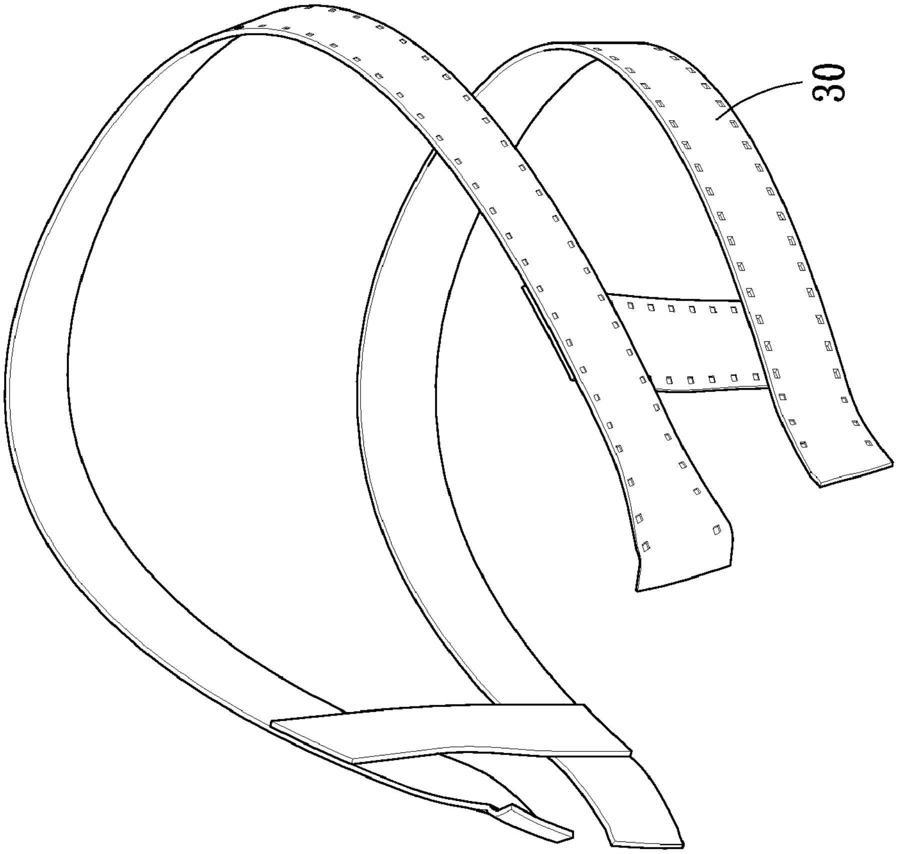
FIG. 5 is a perspective view of an elastic tape of the three dimensional soft rubber washer in accordance with the present invention.

Referring to FIGS. 5 and 2-2, the elastic tape 30 is H-shaped and has two ends symmetrically bonded to both sides of the three dimensional cup 10. When the face mask is worn, the elastic tape 30 elastically wraps around the back of the wearer's head, forcing the three dimensional soft rubber washer 20, the nose cushion 21 and the anti-skid band 40 to closely fit against the face, the nose, and the chin of the wearer, respectively.

While we have shown and described various embodiments in accordance with the present invention, it is clear to those skilled in the art that further embodiments may be made without departing from the scope of the present invention.

What is claimed is:

1. A three dimensional face mask comprising: a three dimensional cup, a three dimensional soft rubber washer, an elastic tape, and an anti-skid band; characterized in that: the three dimensional cup is made by hot pressing of multilayer of filtration material, the three dimensional soft rubber washer is provided with a soft nose cushion and is bonded to an outer periphery of the three dimensional cup by hot pressing, the anti-skid band is bonded to a lower edge of the three dimensional cup, the elastic tape has two ends symmetrically bonded to both sides of the three dimensional cup.

2. The three dimensional face mask as claimed in claim 1, wherein three dimensional cup is protruded outward, and the outer periphery of the three dimensional cup is shaped in an outline of the face of a wearer, leaving a large enough space between the three dimensional cup and the face of the wearer.

3. The three dimensional face mask as claimed in claim 1, wherein the soft nose cushion is fixed to a middle of an upper side of the three dimensional soft rubber washer and made by plastic injection simultaneously with the three dimensional soft rubber washer, the three dimensional soft rubber washer is a ring-shaped structure made by plastic injection, and a shape of the three dimensional soft rubber washer is similar to an outline of the face of a wearer.

4. The three dimensional face mask as claimed in claim 1, wherein the anti-skid band is bonded to the lower edge of the three dimensional cup to naturally form a pocket-like structure.

5. The three dimensional face mask as claimed in claim 1, wherein the elastic tape is H-shaped and has two ends symmetrically bonded to both sides of the three dimensional cup.

6. The three dimensional face mask as claimed in claim 1 further comprising a support frame snuggly fits in the three dimensional cup to provide support for the three dimensional cup and maintain a shape of the three dimensional cup.

7. The three dimensional face mask as claimed in claim 6, wherein the support frame is made of Polypropylene material with high elasticity.

* * * * *